(12) United States Patent
Snow

(10) Patent No.: US 11,207,164 B2
(45) Date of Patent: *Dec. 28, 2021

(54) BIASED ARTIFICIAL SPHINCTER CUFF

(71) Applicant: Boston Scientific Scimed, Inc., Maple Grove, MN (US)

(72) Inventor: Buddy L. Snow, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 32 days.

This patent is subject to a terminal disclaimer.

(21) Appl. No.: 16/404,473

(22) Filed: May 6, 2019

(65) Prior Publication Data

US 2019/0254798 A1  Aug. 22, 2019

Related U.S. Application Data

(63) Continuation of application No. 14/045,224, filed on Oct. 3, 2013, now Pat. No. 10,307,236, which is a continuation of application No. 12/644,504, filed on Dec. 22, 2009, now Pat. No. 8,696,542.

(60) Provisional application No. 61/140,187, filed on Dec. 23, 2008.

(51) Int. Cl.
*A61F 2/00* (2006.01)

(52) U.S. Cl.
CPC .................................... *A61F 2/004* (2013.01)

(58) Field of Classification Search
CPC ........................................... A61F 2/0004–004
See application file for complete search history.

(56) References Cited

U.S. PATENT DOCUMENTS

| | | |
|---|---|---|
| 3,863,622 A | 2/1975 | Buuck |
| 4,705,518 A | 11/1987 | Baker et al. |
| 5,152,770 A | 10/1992 | Bengmark et al. |
| 5,593,443 A | 1/1997 | Carter et al. |
| 5,893,826 A | 4/1999 | Salama |
| 6,074,341 A | 6/2000 | Anderson et al. |

(Continued)

FOREIGN PATENT DOCUMENTS

| | | |
|---|---|---|
| WO | 0000082 A1 | 1/2000 |
| WO | 2007097994 A2 | 8/2007 |

OTHER PUBLICATIONS

Yamamoto, et al., "Optimal parameters for effective electrical stimulation of the anal sphincters in a child with fecal incontinence: preliminary report", Pediatric Surgery International, vol. 8, 1993, pp. 132-137.

(Continued)

*Primary Examiner* — Thaddeus B Cox
(74) *Attorney, Agent, or Firm* — Brake Hughes Bellermann LLP

(57) ABSTRACT

A cuff for use an as artificial sphincter includes an inflatable chamber and a backing. The inflatable chamber includes opposing inside and outside surfaces and inflated and deflated states. The backing is adjacent the outside surface of the chamber. The inside surface of the chamber includes two or more grooves that define the location of fold lines of the inflatable chamber when the inflatable chamber is in the inflated state. The inflatable chamber and backing are configured to surround a duct of a patient with the inside surface of the chamber facing the duct and the grooves extending substantially parallel to the duct.

11 Claims, 7 Drawing Sheets

(56) References Cited

U.S. PATENT DOCUMENTS

| | | |
|---|---|---|
| 6,243,607 B1 | 6/2001 | Mintchev et al. |
| 6,432,038 B1 | 8/2002 | Bakane et al. |
| 6,612,977 B2 | 9/2003 | Staskin et al. |
| 6,659,937 B2 | 12/2003 | Polsky et al. |
| 6,676,674 B1 | 1/2004 | Dudai et al. |
| 6,911,003 B2 | 6/2005 | Anderson et al. |
| 6,966,875 B1 | 11/2005 | Longobardi et al. |
| 7,011,622 B2 | 3/2006 | Kuyava et al. |
| 7,613,516 B2 | 11/2009 | Cohen et al. |
| 2002/0111640 A1 | 8/2002 | Krause et al. |
| 2002/0161382 A1 | 10/2002 | Neisz et al. |
| 2003/0028076 A1* | 2/2003 | Kuyava .................. A61F 2/004 600/29 |
| 2003/0028232 A1 | 2/2003 | Camps et al. |
| 2004/0039453 A1 | 2/2004 | Anderson et al. |
| 2005/0192531 A1 | 9/2005 | Birk |
| 2005/0240144 A1 | 10/2005 | Wassemann et al. |
| 2005/0256367 A1 | 11/2005 | Banik et al. |
| 2006/0135845 A1 | 6/2006 | Kuyava et al. |
| 2007/0015954 A1 | 1/2007 | Dlugos et al. |
| 2007/0021650 A1 | 1/2007 | Rocheleau et al. |
| 2007/0156013 A1 | 7/2007 | Birk et al. |
| 2007/0249893 A1 | 10/2007 | Krumme |
| 2007/0260288 A1 | 11/2007 | Gross et al. |
| 2010/0076254 A1 | 3/2010 | Jimenez et al. |
| 2010/0160716 A1 | 6/2010 | Snow et al. |
| 2011/0015738 A1 | 1/2011 | Vaingast et al. |

OTHER PUBLICATIONS

Yamanishi, et al., "Electrical Stimulation for Stress Incontinence", International Urogynecology Journal, vol. 9, 1998, pp. 281-290.

* cited by examiner

BIASED ARTIFICIAL SPHINCTER CUFF

CROSS-REFERENCE TO RELATED APPLICATIONS

The present application is a continuation of U.S. patent application Ser. No. 14/045,224, filed on Oct. 3, 2013, now U.S. Pat. No. 10,307,236, which is a continuation of U.S. patent application Ser. No. 12/644,504, filed on Dec. 22, 2009, now U.S. Pat. No. 8,696,542, which claims the benefit of U.S. Provisional Patent Application No. 61/140,187, filed on Dec. 23, 2008, the disclosures of which are incorporated by reference herein in their entirety.

BACKGROUND

Incontinence is an affliction that prevents a patient from controlling waste elimination functions. As one might expect, this condition can be quite debilitating and embarrassing and may severely limit the patient's activities.

Various techniques exist for treating incontinence in patients. One such technique is surgical implantation of an artificial sphincter. One form of artificial sphincter includes an appropriately sized inflatable cuff that is positioned around a duct such as either the urethra or the rectum, depending upon the nature of the incontinence. A control pump is fluidly coupled to the cuff and to a pressure-regulating balloon, both of which are positioned within the body of the patient. Under normal conditions, the cuff is inflated which causes a compression of the urethra or the rectum, thus preventing unintentional discharge. When so desired, the patient manually actuates the control pump. Fluid is then withdrawn from the cuff and forced into the pressure-regulating balloon. As this occurs, the cuff relaxes, allowing the urethra or rectum to expand and open. At this point, normal waste elimination functions are permitted. The pressure-regulating balloon contains a volume of fluid that is maintained at a relatively high pressure. The control pump is provided with a fluid resistor that allows pressurized fluid from the balloon to slowly return to the cuff causing it to automatically re-inflate.

One such artificial sphincter or inflatable cuff employs a generally rectangular inflatable member that is wrapped about the outer circumference of the duct and the ends are connected together. As pressure is increased and the cuff inflates, the interior area defined by the cuff is compressed, thus achieving the desired results. The cuff may be formed from silicone, which has proven to be a reliable and medically safe material that is usually compatible with human tissue.

Due to the nature and configuration of the rectangular chamber that forms the cuff, a non-continuous geometrical configuration is produced. That is, the wall of the cuff which forms the interior circumference, (i.e., that which is in contact with the duct), has one or more fold lines that develop. In some instances, the fold lines form in a triangular configuration so as to apply pressure to multiple sides of the urethra or rectum. At smaller sizes, the chamber may be prevented from forming a triangular configuration when wrapping around the urethra or rectum. Instead, the chamber can be disposed to create a single fold line proximate a center of the chamber. This configuration can lead to undesired discharge through the duct as well as abrasion, wear and fatigue of the duct and/or inflatable chamber.

SUMMARY

Embodiments of the invention are directed to an artificial sphincter system and a cuff for use an as artificial sphincter in such a system. One embodiment of the cuff comprises an inflatable chamber and a backing. The inflatable chamber includes opposing inside and outside surfaces and inflated and deflated states. The backing is adjacent the outside surface of the chamber. The inside surface of the chamber includes two or more grooves that define the location of fold lines of the inflatable chamber when the inflatable chamber is in the inflated state. The inflatable chamber and backing are configured to surround a duct of a patient with the inside surface of the chamber facing the duct and the grooves extending substantially parallel to the duct.

On embodiment of the artificial sphincter system comprises a balloon, a cuff and a control pump. The cuff comprises an inflatable chamber and a backing. The inflatable chamber includes opposing inside and outside surfaces and inflated and deflated states. The backing is adjacent the outside surface of the chamber. The inside surface of the chamber includes two or more grooves that define the location of fold lines of the inflatable chamber when the inflatable chamber is in the inflated state. The control pump is fluidically coupled to the balloon and the cuff.

This Summary is provided to introduce a selection of concepts in a simplified form that are further described below in the Detailed Description. This Summary is not indented to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION

Figure 1:
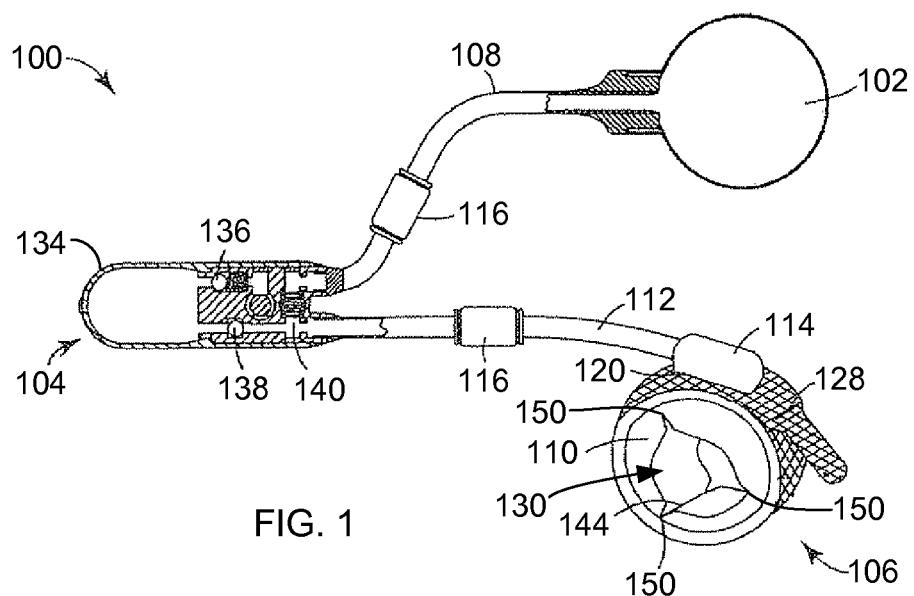
FIG. 1 is a simplified diagram of an artificial sphincter system in accordance with embodiments of the invention.
Figure 2:
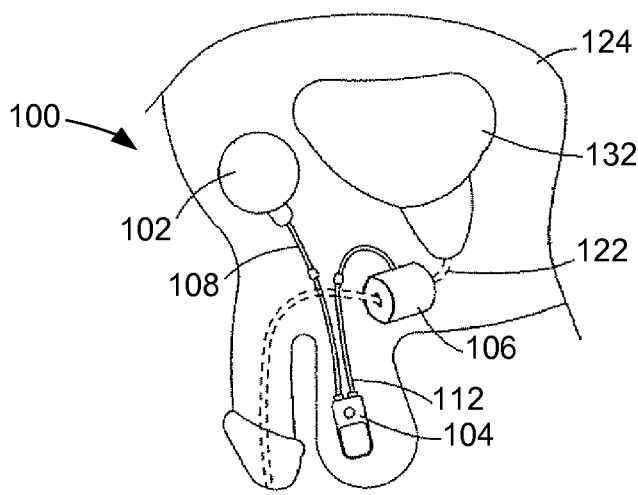
FIG. 2 illustrates an exemplary implantation of the artificial sphincter system in a male patient to control a flow through the urethra of the patient.

Embodiments of the invention are directed to an implantable artificial sphincter system 100, illustrated in FIGS. 1 and 2, that is configured to control a flow through a duct of a patient. FIG. 1 illustrates some components of the system 100 in cross-section while oblique views are provided of other components. FIG. 2 illustrates an exemplary implantation of the system 100 in a male patient to control a flow through the urethra of the patient and treat urinary incontinence. It is understood that the system 100 may be used to control flows through other ducts of male and female patients, such as the rectum to treat fecal incontinence, and other ducts.

Embodiments of the system 100 include one or more of the components depicted in FIG. 1 including a pressure-regulating balloon 102, a control pump 104, and an inflatable cuff 106. The pressure-regulating balloon 102 is fluidically coupled to the control pump 104 via a tube 108. The inflatable cuff 106 includes an inflatable chamber 110, which is fluidically coupled to the control pump 104 by a second tube 112. The second tube 112 connects to the inflatable chamber 110 via a suitable adapter 114. The tubes 108 and 112 are separable at connectors 116 to simplify the implantation of the system 100 in the patient.

In one embodiment, some of the components of the cuff 106, such as the inflatable chamber 110, are formed from silicone, which has proven to be a reliable and medically safe material that is usually compatible with human tissue. Other biocompatible materials may also be used for the components of the cuff 106.

One embodiment of the cuff 106 includes a backing 120. In one embodiment, the backing 120 is attached to the inflatable chamber 110, such as with an adhesive, for example. In accordance with another embodiment, the backing 120 is disconnected from the chamber 110.

Figure 3:
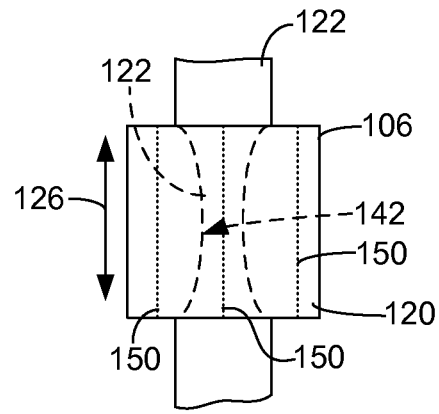
FIG. 3 is a top view of a cuff formed in accordance with embodiments of the invention installed around a duct.

In one embodiment, the backing 120 can be used to secure the cuff 106 around a duct 122 of the patient, such as the urethra within the patient's abdomen 124, as illustrated in FIG. 2. A widthwise direction (arrow 126), which is defined by the width of the inflatable chamber 110 and the backing 120, is generally aligned parallel to the duct 122, as shown in FIG. 3, which is a top view of the cuff 106 installed around the duct 122. In one embodiment, as the cuff 106 is wrapped around the duct 122, the adapter 114 and a portion of the tube 112 are passed through a backing slit 128 within a backing 120 to hold the cuff 106 in position on the duct 122. The tube 112 can be coupled to the control pump 104 via the connector 116 after the cuff 106 is installed on the duct 122.

The system 100 contains a volume of fluid that is sufficient to cause an expansion of the balloon 102 when the system is in a quiescent state. The expanded state of the balloon 102 pressurizes the fluid in the system 100 and maintains the chamber 110 of the cuff 106 in the desired inflated state. The backing 120 is configured so that upon inflation of the cuff 106, expansion of the chamber 110 occurs inwardly toward the duct 122. The inflated chamber 110 constricts the interior area 130 (FIG. 1) defined by the cuff 106 and compresses the duct 122, to prevent a flow through the duct 122, as shown in FIG. 3. Thus, the inflated state of the cuff 106 can inhibit urinary incontinence when the cuff 106 is implanted around the urethra (FIG. 2) of the patient, or fecal incontinence when the cuff 106 is inflated around the rectum of the patient, for example.

When the patient desires to allow a flow through the duct 122, such as to void the bladder 132 (FIG. 2), the patient manually actuates the control pump 104 by compressing a bulb 134. The compression of the bulb 134 drives the fluid contained within the bulb 134 through an outflow check valve 136 and into the balloon 102. When the bulb 134 is released, the outflow check valve 136 closes and an inflow check valve 138 will open, due to a generated vacuum within the bulb 134 responsive to the bulb 134 transitioning back to its expanded quiescent shape. A flow of fluid from the chamber 110 of the cuff 106 travels through the inflow check valve 138 and into the bulb 134 as the bulb 134 expands. This compression and expansion of the bulb 134 is repeated to sufficiently deflate the chamber 110 and allow the duct 122 to expand and allow a flow through the duct 122. As a result, this deflated state of the cuff 106 allows for normal waste voiding of the bladder 132 or rectum depending on the duct 122 being controlled.

In one embodiment, the pressure-regulating balloon 102 is in fluid communication with the cuff 106 through a fluid resistor 140. The fluid resistor 140 operates to resist the flow of fluid from the balloon 102 to the cuff 106 and block the flow of fluid from the cuff 106 to the balloon 102. Thus, when the cuff 106 is in the deflated state, the fluid pressure in the balloon 102 is higher than the fluid pressure in the cuff 106 and fluid flows from the balloon 102 to the cuff 106 through the fluid resistor 140. Over time, fluid from pressure-regulating balloon 102 will seep through fluid resistor 140 and automatically re-inflate cuff 106. The restrictive flow of fluid through the resistor 140 is sufficiently slow to allow the cuff 106 to reach the desired deflated state through the actuation of the bulb 134.

In one embodiment, the control pump 104 utilizes an electrical pump that can be activated through the pressing of a button on the control pump 104 or remotely.

Referring again to FIG. 1, the chamber 110 forms the interior of the cuff 106. Despite being wrapped in a generally circular configuration, an inside surface 142 of the chamber 110 that faces the duct 122 and may be in direct contact with the duct 122, is generally not circular in nature. Rather, the surface 142 forms a non-continuous, noncircular geometrical configuration. That is, the surface 142 has a series of fold lines 144 that develop. At each termination of a fold line 144 exists a fold corner.

In one embodiment, the cuff 106 includes a biasing mechanism that operates to bias the chamber 110 in a desired configuration so as to create the fold lines 144 in the chamber 110 at desired positions when the cuff 106 is installed around a duct 122 and the chamber 110 is in the inflated state. In one embodiment, the biasing mechanism includes a plurality of grooves 150 that are formed in a wall of the chamber 110 and/or the backing 120, as indicated in FIG. 3. The grooves 150 operate to predefine the location of the fold lines of the surface 142 of the chamber 110 that faces the duct 122. As used herein, the term "grooves" describes a designed feature of the inflatable chamber 110 and/or the backing 120 that determines the location of the fold lines 144 in the chamber 110 when the chamber 110 is in the inflated state around the duct 122. In one embodiment, the grooves 150 are substantially parallel to the widthwise direction 126 and the duct 122 when the cuff 106 is installed around the duct 122, as illustrated in FIG. 3.

In one embodiment, the grooves 150 bias the chamber 110 to have three fold lines 144 and direct the chamber 110 into a generally triangular inflated state configuration, as shown in FIG. 1. Additional embodiments include inflated state configurations of the chamber 110 that are generally square, pentagonal, hexagonal, octagonal, circular, and other geometric shapes.

FIGS. 4-7 are schematic diagrams of cuffs formed in accordance with additional embodiments of the invention that can be used in the system 100 described above. FIG. 4A is a simplified side view of a cuff 160 in accordance with embodiments of the invention and FIG. 4B is a simplified bottom view of the cuff 160 shown FIG. 4A. FIG. 4C is a simplified side view of the cuff 160 in an operational position in which it surrounds a duct 122 (illustrated in phantom) of a patient. The cuff 160 includes a generally elongated rectangular chamber 162 and a backing 164. The chamber 162 is preferably attached to the backing 164, but may be detached from the backing 164.

In one embodiment, the backing 164 comprises a flexible member 166 and one or more rigid or reinforcing members 168 that are attached to the flexible member 166. The flexible member 166 can be of any suitable implantable material that is generally configured to bend around the duct 122, as shown in FIG. 4C. Embodiments of the flexible member 166 include a strap of suitable biocompatible material.

The rigid members 168 are more stiff than the flexible member 166 and resist bending when the cuff 160 is installed around the duct 122. The rigid members 168 can be formed of any suitable biocompatible material, such as plastic, metal or other material. In one embodiment, the rigid members 168 are formed of a silicone elastomer reinforced with polyester yarn.

The rigid members 168 are displaced from each other along a length of the backing 164 and create a plurality of regions or grooves 150 located just outside of the rigid members 168 and between adjacent rigid members 168. These grooves 150 define fold lines 144, at which the backing 164 will fold when the cuff 160 is installed around a duct 122, as shown in FIG. 4C. Thus, the grooves 150 bias the cuff 160 into a specific configuration when installed around the duct 122 and controls the inflated state configuration of the chamber 162.

Figure 4A:
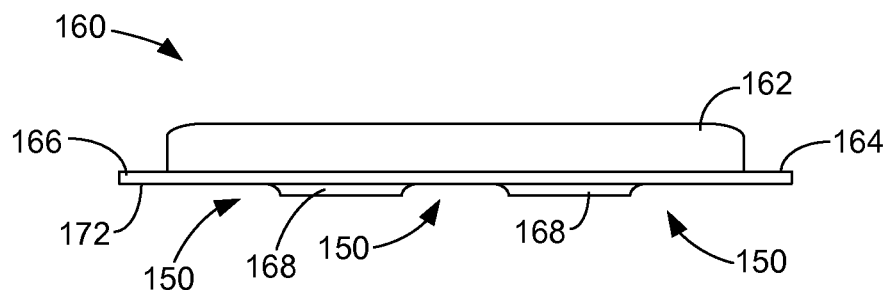
FIGS. 4A and 4B respectively are simplified side and bottom views of a cuff in accordance with embodiments of the invention.
Figure 4B:
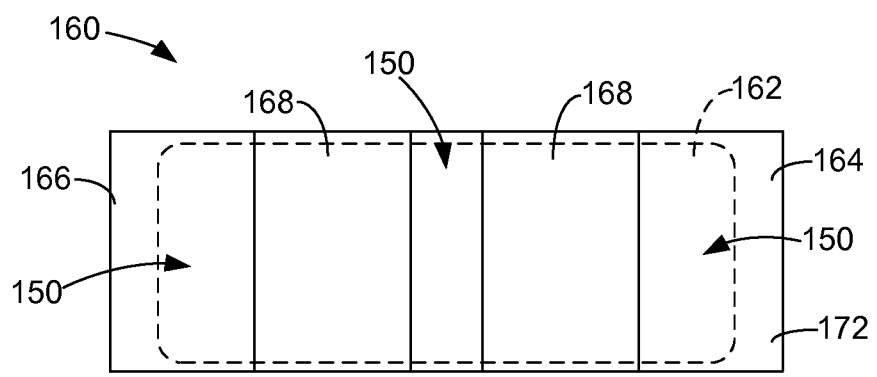
Figure 4C:
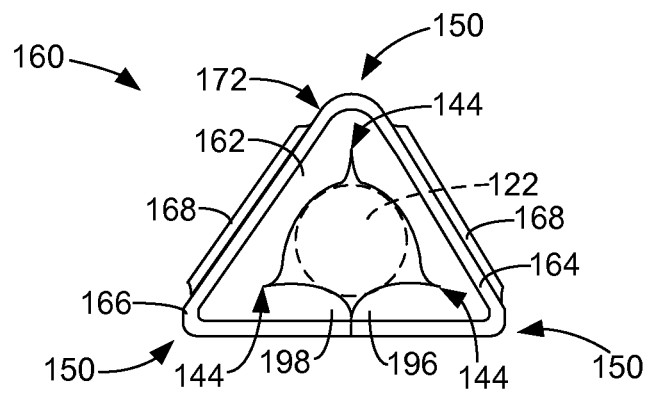
FIG. 4C is a simplified front view of the cuff shown in FIGS. 4A and 4B in an operational position, in which it surrounds a duct of a patient.

In one embodiment, the rigid members 168 are attached to an outside surface 172 of the flexible member 166, as shown in FIGS. 4A-C. The rigid members 168 operate as discussed above to define the fold lines 144 of the backing 164 when the cuff 160 is in an inflated state around the duct 122, as shown in FIG. 4C.

Figure 4D:
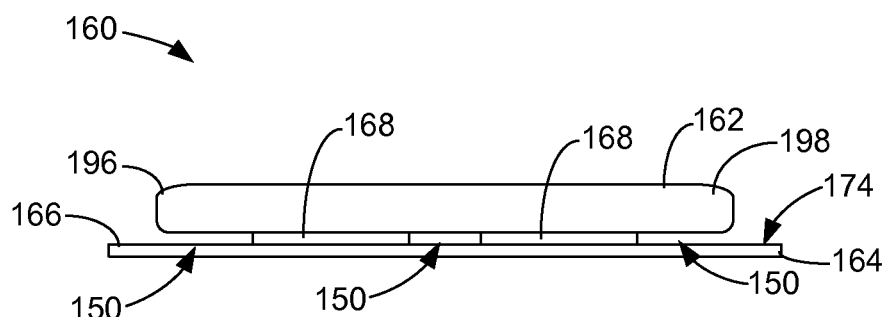
FIG. 4D is a simplified side view of a cuff in accordance with embodiments of the invention.

In accordance with another embodiment, the rigid members 168 are disposed on an interior surface 174 of the flexible member 166, and between the flexible member 166 and the chamber 162, as illustrated in the side view of the cuff 160 provided in FIG. 4D. In yet another embodiment, the rigid members 168 are disposed within the flexible member 166 or between flexible members 166, as shown in the partial cross-sectional view of the cuff 160 provided in FIG. 4E.

In one embodiment, the cuff 160 includes two rigid members 168, which operate to direct the backing 164 into a generally triangular configuration when folded around the duct 122 of a patient, as shown in FIG. 4C.

Figure 4E:
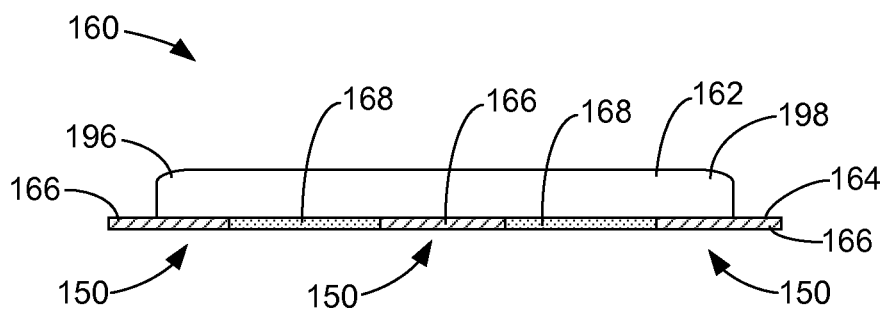
FIG. 4E is a simplified side view of a cuff in accordance with embodiments of the invention, with a backing illustrated in cross-section.
Figure 4F:
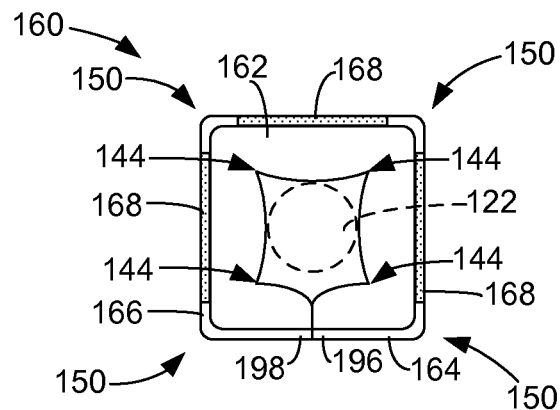
FIG. 4F is a simplified front view of the cuff of FIG. 4E in operation around a duct of a patient.

Additional embodiments of the cuff 160 include more than two rigid members 168 to bias the cuff 160 into other shapes when placed around the duct 122 of a patient. In one embodiment, the cuff 160 includes three rigid members 168 to place the cuff 160 into a generally square inflated state configuration, as shown in FIG. 4F. Additional embodiments of the cuff 160 include four rigid members 168 to place the cuff 160 into a generally pentagonal inflated state configuration, five rigid members 168 to place the cuff 160 into a generally hexagonal inflated state configuration, and more than five rigid members 168 to place the cuff 160 into other inflated state configurations, such as heptagonal, octagonal, etc.

Figure 5A:
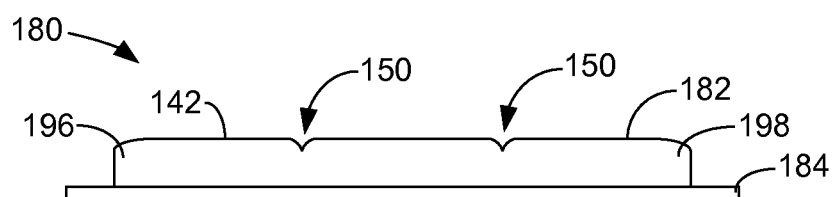
FIGS. 5A and 5B respectively show side and top plan views of a cuff formed in accordance with embodiments of the invention.
Figure 5B:
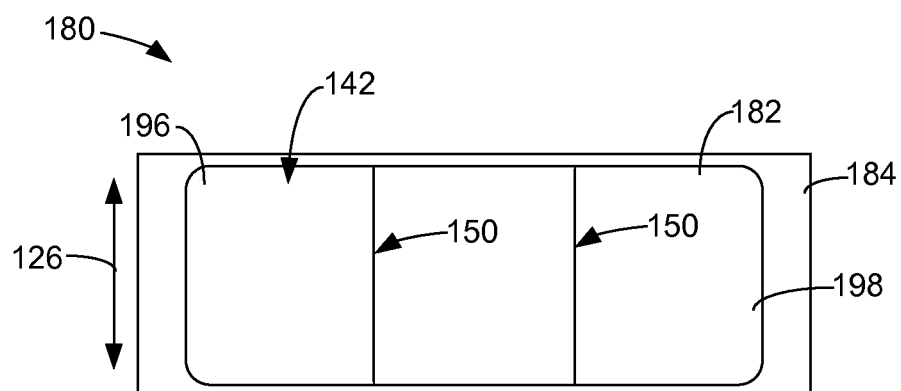

FIGS. 5A and 5B respectively show side and top plan views of a cuff 180 formed in accordance with embodiments of the invention. The cuff 180 includes an inflatable chamber 182 and a backing 184. A plurality of grooves 150 are formed in an interior wall 142 of the chamber 182. The plurality of grooves 150 include at least two grooves 150 that extend in a widthwise direction 126 that is approximately parallel with the duct 122 when the cuff 180 is installed around the duct 122, as illustrated in FIG. 5B. The chamber 182 with the grooves 150 can be formed using a dip molding or injection molding process, for example.

The grooves 150 of the chamber 182 operate as the biasing mechanism that biases the chamber 182 into a desired inflated state configuration by encouraging fold lines 144 at each of the grooves 150. When chamber 182 is folded around the duct 122, the chamber 182 will fold at the lines where grooves 150 are positioned.

For the exemplary embodiment of the cuff 180 having two grooves 150 shown in FIGS. 5A and 5B, the inflated state configuration of the chamber 182 is triangular, similar to that shown in FIG. 4C. When the cuff 180 includes three grooves 150, the inflated state configuration of the chamber 182 approximates a square. Additional grooves 150 can bias the chamber 182 into pentagonal, hexagonal, heptagonal, octagonal, etc.

Figure 5C:
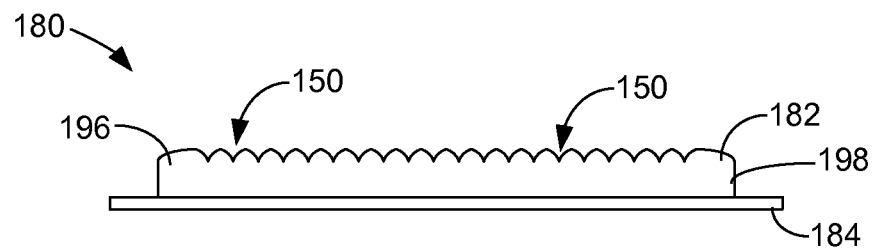
FIG. 5C is a side plan view of a cuff formed in accordance with embodiments of the invention.
Figure 5D:
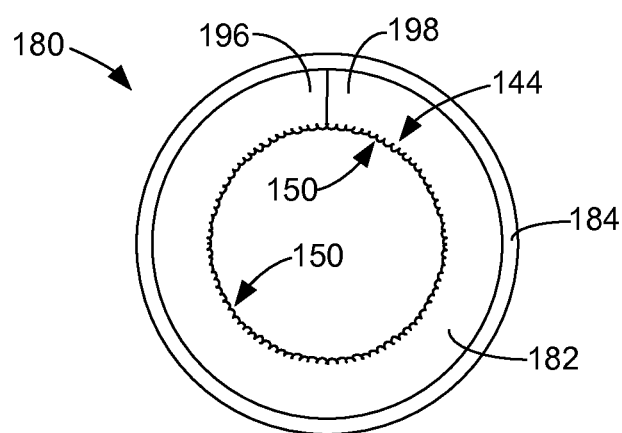
FIG. 5D is a front view of a cuff having a high number of grooves installed around a duct of a patient.

FIG. 5C is a side plan view of the cuff 180 having a high number of the grooves 150 on the interior surface 142 of the chamber 182 than that illustrated in FIGS. 5A-B. The number of grooves 150 on a chamber 182 can be set based upon the desired inflated state configuration of the chamber 182. Embodiments of the cuff 180 include one, two, three, five, ten, twenty or more grooves 150 on the surface 142 of the chamber 182. In one embodiment, the number of grooves 150 per centimeter of the chamber 182 can be in a range of 0.2 grooves per centimeter to twenty grooves per centimeter, for example. In one embodiment, the chamber 182 has at least 0.5 grooves/cm. In another embodiment, the chamber 182 has at least 10 grooves/cm. The plurality of grooves 150, create a bias mechanism to encourage fold lines 144 at desired positions in the chamber 182 at the grooves. When the cuff 180 includes many grooves 150, the inflated state configuration of the chamber 182 is more circular when the cuff 180 is installed around a duct, as shown in the front view of FIG. 5D.

Figure 6A:
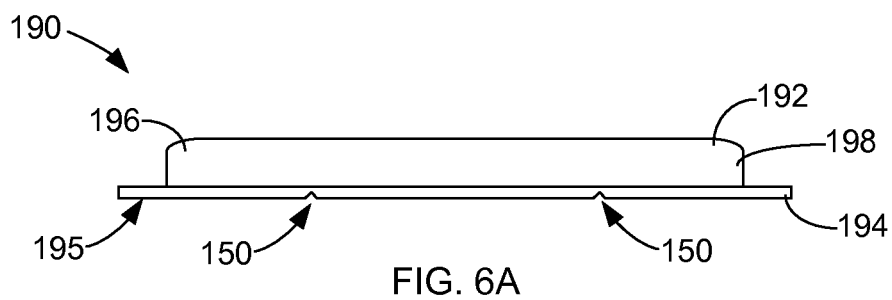
FIGS. 6A and 6B are side and bottom views of a cuff m accordance with embodiments of the invention.
Figure 6B:
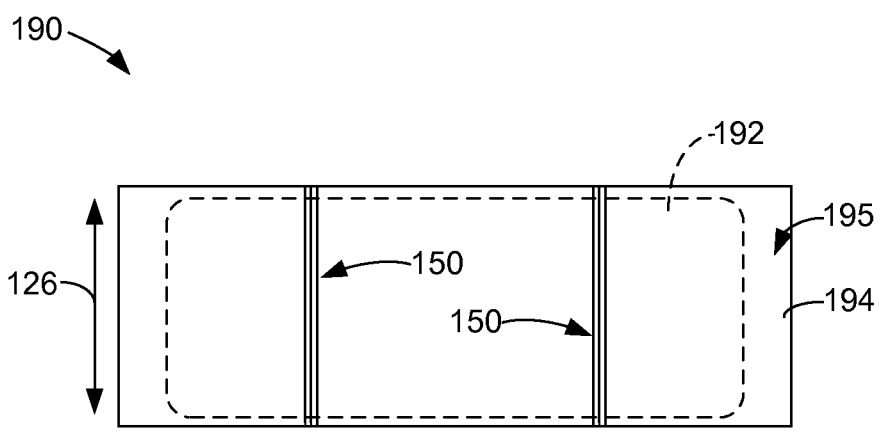

FIGS. 6A and 6B are side and bottom views of a cuff 190 in accordance with embodiments of the invention. The cuff 190 generally comprises an inflatable chamber 192 and a backing 194. In one embodiment, the inflatable chamber 140 is formed in accordance with the chamber 182 described above and includes the grooves 150. In one embodiment, the chamber 192 does not include the grooves 150.

In one embodiment, the backing 194 is attached to the inflatable chamber 192, such as with an adhesive, for example. In accordance with another embodiment, the backing 194 is disconnected from the chamber 192.

In one embodiment, the backing 194 is formed of a rigid or semi-rigid body. An outside surface 195 of the backing 194 includes a plurality of grooves 150. The grooves 150 extend in the widthwise direction 126 of the cuff 190 to place the grooves 150 in substantially parallel alignment with the duct 122 when the cuff 190 is installed around the duct 122. The grooves 150 operate as a biasing mechanism that drives the inflated state configuration of the cuff 190. In particular, the grooves 150 define weaker sections of the backing 194 where the backing will bend as the inflatable chamber 192 inflates around the duct 122. The grooves 150 can be generated in various ways understood by those skilled in the art. For instance, the grooves 150 can be formed in the backing 194 by including the grooves 150 in the die used to form the backing 194. The grooves 150 may also be formed in the backing 194 by cutting or stamping the backing 194, or other suitable method. As mentioned above, the number of grooves 150 can be selected as desired.

Because the grooves 150 determine the fold lines 144 in the inflatable chamber, the distance separating adjacent grooves 150 determines the distance of one side of the inflated state configuration of the chamber. In one embodiment, the grooves 150, or the fold lines 144 that are formed responsive to the location of the grooves 150, are equally spaced from each other along the length of the inflatable chamber. When the cuff is installed around a duct 122, end portions 196 and 198 of the chamber can be joined together to form a side of the inflated state configuration of the chamber, as shown in FIGS. 4C and 4E. In one embodiment, the distance from the ends 196 and 198 of the chamber 182 to the nearest groove 150 is approximately one half the distance separating adjacent grooves 150. As a result, the side of the chamber formed by abutting the ends 196 and 198 together when the cuff is installed around a duct 122 has a length that is approximately equal to the distance separating adjacent grooves 150.

Figure 7A:
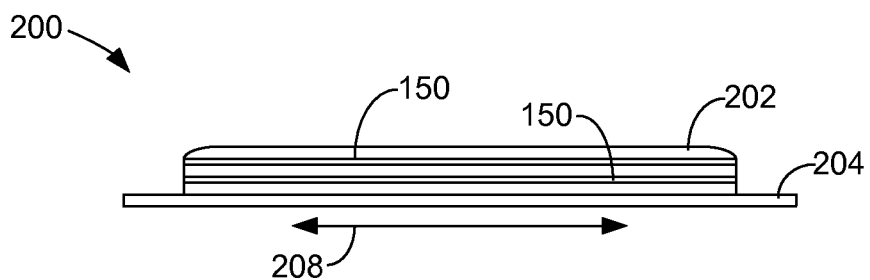
FIGS. 7A and 7B illustrate side and cross-sectional views of a cuff in accordance with embodiments of the invention.
Figure 7B:
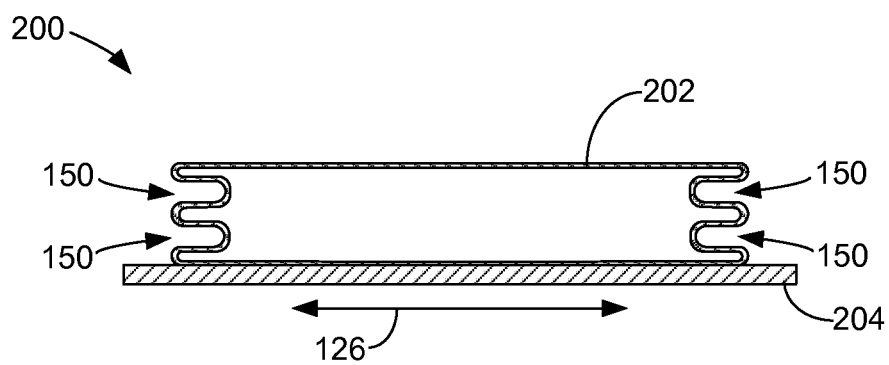

FIGS. 7A and 7B illustrate side and cross-sectional views of a cuff 200 in accordance with embodiments of the invention. In one embodiment, the cuff 200 includes an inflatable chamber 202. In one embodiment, the cuff 200 includes a backing 204 that may be attached to the chamber 202 or detached from the chamber 202. One embodiment of the chamber 202 includes one or more folds or grooves 150 that extend in a lengthwise direction 208, which is opposite the widthwise direction 126 along the chamber 202. As a result, the grooves 150 run substantially perpendicular to duct 122 when the cuff 200 is installed around the duct 122. In one embodiment, the grooves 150 cooperate to create a bias mechanism that encourages fold lines at desired positions along the grooves. When folded around the urethra, or other duct, the inflated state configuration of the cuff 200 will be approximately circular.

Embodiments of the invention include a cuff formed in accordance with one or more of the embodiments described above. Additional embodiments include an artificial sphincter system utilizing the cuff formed in accordance with embodiments of the invention. The cuff includes a biasing mechanism that includes one or more grooves that generally define fold lines in the inflated state configuration of the cuff when implanted around a duct of a patient. The grooves can be applied to a backing of the cuff and/or to an inflatable chamber of the cuff to encourage the desired fold lines. Grooves in the chamber are generally formed parallel to the duct, but the chamber can also include grooves that are non-parallel to the duct.

Although the concepts presented herein have been described with reference to particular embodiments, workers skilled in the art will recognize that changes may be made in form and detail without departing from the spirit and scope of the following claims. The cuffs presented herein are exemplary and various aspects of the cuffs can be modified as desired. For example, the cuffs can have dimensions that are suitable for the desired application of the cuff. Additionally, it is understood that the figures are generally simplified illustrations that are not drawn to scale.

What is claimed is:

1. An apparatus, comprising:
an inflatable chamber having an inside surface, an outside surface opposite the inside surface, an inflated state, and a deflated state; and
a backing adjacent the outside surface of the inflatable chamber, the backing including a flexible member, a first reinforcing member, and a second reinforcing member, the first reinforcing member being disposed apart from the second reinforcing member, the first reinforcing member being more stiff than the flexible member and being configured to resist bending, the backing defining a groove disposed between the first reinforcing member and the second reinforcing member;
wherein the groove defines the location of a fold line when the inflatable chamber is in the inflated state; and
the inflatable chamber and backing are configured to surround a duct of a patient with the inside surface of the inflatable chamber facing the duct and the groove extending substantially parallel to the duct.

2. The apparatus of claim 1, wherein the backing includes two grooves configured to bias the inflatable chamber into a triangular shape when installed around the duct.

3. The apparatus of claim 1, wherein the backing includes three grooves, each configured to define a fold line when the inflatable chamber is in the inflated state.

4. The apparatus of claim 1, wherein the backing includes at least five grooves.

5. The apparatus of claim 1, wherein the backing includes at least ten grooves.

6. The apparatus of claim 1, wherein the inflatable chamber is attached to the backing.

7. The apparatus of claim 1, wherein the first reinforcing member is formed of a silicone elastomer reinforced with polyester yarn.

8. The apparatus of claim 1, wherein the first reinforcing member is attached to a surface of the flexible member.

9. The apparatus of claim 1, wherein the inflatable chamber and backing are configured to surround a duct of a female patient.

10. The apparatus of claim 1, wherein the inflatable chamber and backing are configured to surround a urethra of a patient.

11. The apparatus of claim 1, wherein the inflatable chamber and backing are configured to surround a rectum of a patient.

* * * * *